United States Patent [19]

Boon et al.

[11] Patent Number: Plant 6,419

[45] Date of Patent: Nov. 22, 1988

[54] LILY PLANT NAMED HILDE

[75] Inventors: Jacobus A. J. Boon, Venhuizen; Albertus J. Boon, Hem; Petrus T. Boon, Venhuizen, all of Netherlands

[73] Assignee: De vennootschap onder firma Jaap Boon, Hem, Netherlands

[21] Appl. No.: 16,118

[22] Filed: Feb. 18, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Evans

[57] ABSTRACT

A new lily plant named Hilde characterized by its yellow tepals, sturdy stems, excellent disease resistance, retention of buds, excellent bulb production, good shipping qualities, and its ability to be grown in sub-tropical areas with higher soil temperatures.

1 Drawing Sheet

The present invention comprises a new and distinct cultivar of lily, botanically known as Lilium (Asiatic Hybrid) and hereinafter referred to by the cultivar name Hilde.

Hilde is a product of a planned breeding program, which had the objective of creating new lily cultivars which flower throughout the year.

Hilde was originated by applicants from a hybridization made in a controlled breeding program in Hem, The Netherlands. The seed or female parent was the cultivar resulting from the cross of Pirate×the cultivar designated L69-12-78. The male or pollen parent was the cultivar Milk & Honey.

Hilde was discovered and selected by applicants as one flowering plant within the progeny of the stated cross in 1977 in a controlled environment in Hem, The Netherlands.

The first act of asexual reproduction of Hilde was accomplished by scaling of the bulbs of the initial selection in the autumn of 1977 in a controlled environment in Hem by applicants. Horticultural examination of selected units initiated by the Plant Breeders' Rights Office in The Netherlands in September 1982 has demonstrated that the combination of characteristics as herein disclosed for Hilde are firmly fixed and are retained through successive generations of asexual reproduction.

Hilde has not been observed under all possible environmental conditions. The phenotype may vary significantly with variations in environment such as temperature, light intensity, and day length. The following observations, measurements, and comparisons describe plants grown in Hem/Aalsmeer, The Netherlands under greenhouse conditions which approximate those generally used in commercial practice.

The following traits have been repeatedly observed and are determined to be basic characteristics of Hilde which in combination distinguish this lily as a new and distinct cultivar:

1. Hilde has yellow flowers, with only a few spots at the base (approximately 0–5 per flower).
2. The cultivar has good, sturdy stems, including the winter period.
3. Depending on the climate, the height is between 90 and 140 centimeters.
4. The cultivar has 3 to 5 well colored buds when the first bud opens, and yellow tepals.

5. Hilde is insensitive to leaf-scorch.
6. The tendency to drop buds is very slight, including the period from December 15 to September 15 without special growing techniques.
7. Cultivation in sub-tropical areas with higher soil temperature has been very good to date.
8. The processing and shipping of plants as cut flowers is excellent. The cultivar can be transported well without water.
9. Harvesting of bulbs is excellent since the cultivar produces substantial and sturdy bulbs.
10. The height of plants grown outside is between 70 and 100 centimeters.
11. To date, Hilde has shown little sensitivity to virus diseases, fusarium and botrytis.

Of the many lily cultivars known to applicants, there is no cultivar sufficiently similar and from which meaningful comparisons can be made.

The accompanying photographic drawing shows typical flower characteristics of Hilde, with colors being as true as possible with illustrations of this type. In the following description, color references are made to The Royal Horticultural Society Color Chart. The color values were determined between 2:00 p.m. and 3:00 p.m. on May 25, 1983 in greenhouses at Hillegom, The Netherlands.

Plant: *Height (at anther dehiscence of the first flower)*-.—Medium.

Stem:
- *Anthocyanin coloration.*—Present, brown/purple.
- *Color.*—Medium green.
- *Pubescence.*—Present but weak.
- *Type of hairs.*—Long.
- *Distribution of pubescence.*—Predominantly in the leaf axils.
- *Length of internode.*—Uniform.
- *Cross section.*—Ribbed but weak.
- *Bulbils.*—Absent.

Leaf:
- *Arrangement.*—Alternate.
- *Upper angle of base with stem.*—Acute.
- *Length.*—Medium.
- *Width.*—Narrow.
- *Thickness.*—Normal.
- *Shape (middle third of stem).*—Narrow elliptic.
- *Color of upper side.*—Dark green.

*Glossiness of upper side.*—Medium.
*Apex.*—Acute.
*Uniformity of shape.*—Present.
*Cross section.*—Flat.
*Distal part.*—Straight.
*Flexibility.*—Strong.

Inflorescence:
*Type.*—Racemose.
*Flowers of secondary order.*—Absent.
*Pubescence.*—Present.
*Bracts.*—Present, equal to number of primary flowers.
*Bracteols.*—Present, equal to number of flowers.

Flower:
*Attitude.*—Erect.
*Type.*—Bowl-shaped.
*Diameter.*—Medium.
*Depth of corolla.*—Medium.
*Length of longest pedicel.*—Medium.
*Length of longest outer tepal.*—Medium.
*Width of widest outer tepal.*—Medium.
*Length of longest inner tepal.*—Medium.
*Width of widest inner tepal.*—Medium.
*Color of inner side of inner tepal.*—14B/12A.
*Color of outer side of inner tepal.*—14B/10A.
*Color of inner side of outer tepal.*—14B/12A.
*Color of outer side of outer tepal.*—14B/12B.
*Markings of inner side.*—Dark brown spots, sparse.
*Color of inner side of throat.*—10B.
*Color of outer side of throat.*—10B.
*Texture of inner side of flower.*—Ribbed and papillose.
*Undulation of tepal margin.*—Present, coarse.

*Curving of tepal.*—Tips slightly recurved.
*Scent.*—None.

Stamens:
*Length.*—Medium.
*Color of filaments.*—Yellow.
*Color of anthers.*—Orange.

Pollen:
*Color.*—Orange.

Pistil:
*Length.*—Medium.

Style:
*Color.*—Yellow.

Stigma:
*Color.*—Red-purple.

Bulb:
*Type (in dormant season).*—Type 2.
*Apex.*—Pointed.
*Density of scales.*—Dense.
*Color of outer scales.*—White and purple.
*Apex of scales.*—Pointed.

Underground part of stem:
*Bulblets.*—Present.
*Roots.*—Present.

We claim:

1. A new and distinct cultivar of lily plant named Hilde, as described and illustrated, and particularly characterized as to uniqueness by its yellow tepals, sturdy stems, excellent disease resistance, retention of buds, excellent bulb production, good shipping qualities, and its ability to be grown in sub-tropical areas with higher soil temperatures.

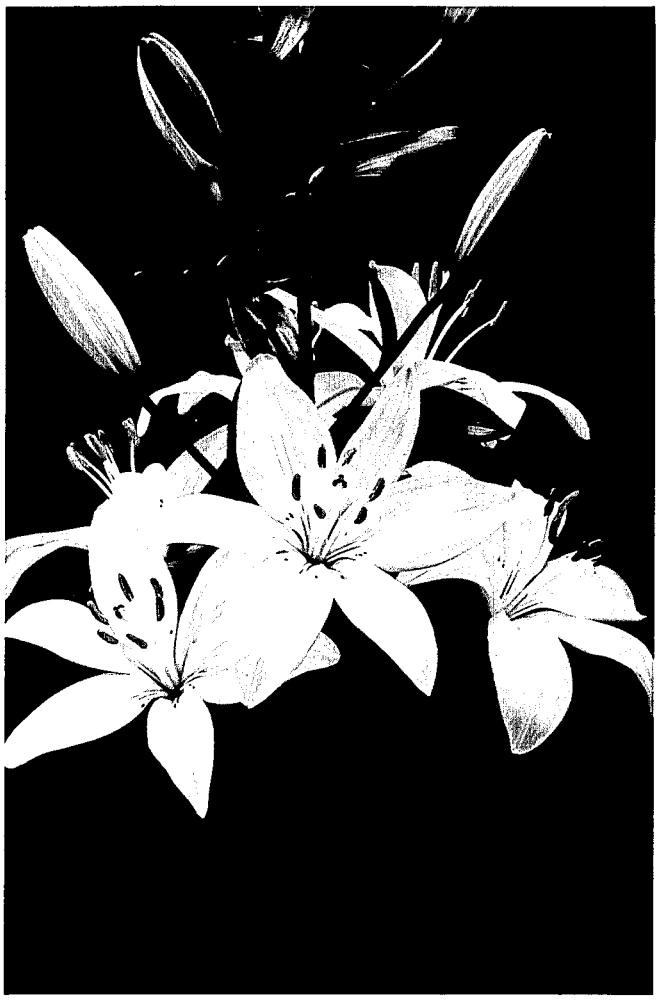

* * * * *